United States Patent
Argese et al.

(10) Patent No.: US 6,653,470 B1
(45) Date of Patent: Nov. 25, 2003

(54) PROCESS FOR THE PREPARATION OF 1,4,7,10-TETRAAZACYCLODODECANE

(75) Inventors: Maria Argese, Milan (IT); Giuseppe Manfredi, Milan (IT); Fabrizio Rebasti, Milan (IT); Giorgio Ripa, Milan (IT)

(73) Assignee: Bracco International B.V., Amsterdam (NL)

( * ) Notice: Subject to any disclaimer, the term of this patent is extended or adjusted under 35 U.S.C. 154(b) by 0 days.

(21) Appl. No.: 09/914,876

(22) PCT Filed: Mar. 6, 2000

(86) PCT No.: PCT/EP00/01867

§ 371 (c)(1), (2), (4) Date: Oct. 11, 2001

(87) PCT Pub. No.: WO00/53588

PCT Pub. Date: Sep. 14, 2000

(30) Foreign Application Priority Data

Mar. 9, 1999 (IT) .......................................... MI99A0474

(51) Int. Cl.[7] ................... C07D 257/02; C07D 487/22; C07D 487/16

(52) U.S. Cl. .................. 540/474; 544/343; 544/346
(58) Field of Search ........................................... 540/476

(56) References Cited

FOREIGN PATENT DOCUMENTS

| WO | WO 96/28432 | * | 9/1996 |
| WO | WO 97/49691 | * | 12/1997 |
| WO | WO 98/49151 | * | 11/1998 |

OTHER PUBLICATIONS

G. Herve et al.: "Condensation of glyoxal with triethylenetetramine. Stereochemistry, cyclization and deprotection," Tetrahedron Letters. 40(13):2517–2520 (1999).*

* cited by examiner

*Primary Examiner*—Mark L. Berch
*Assistant Examiner*—Kahsay Habte
(74) *Attorney, Agent, or Firm*—Nixon & Vanderhye P.C.

(57) ABSTRACT

1,4,7,10-Tetraazacyclodecane, a precursor for the synthesis of macrocylic chelating agents for metal ions such as gadolinium, is prepared efficiently as a highly pure product on an industrial scale.

8 Claims, No Drawings

PROCESS FOR THE PREPARATION OF 1,4,7,10-TETRAAZACYCLODODECANE

The present invention relates to a novel process for the preparation of 1,4,7,1-tetraazacyclododecane (I) comprising the steps represented in Scheme 1.

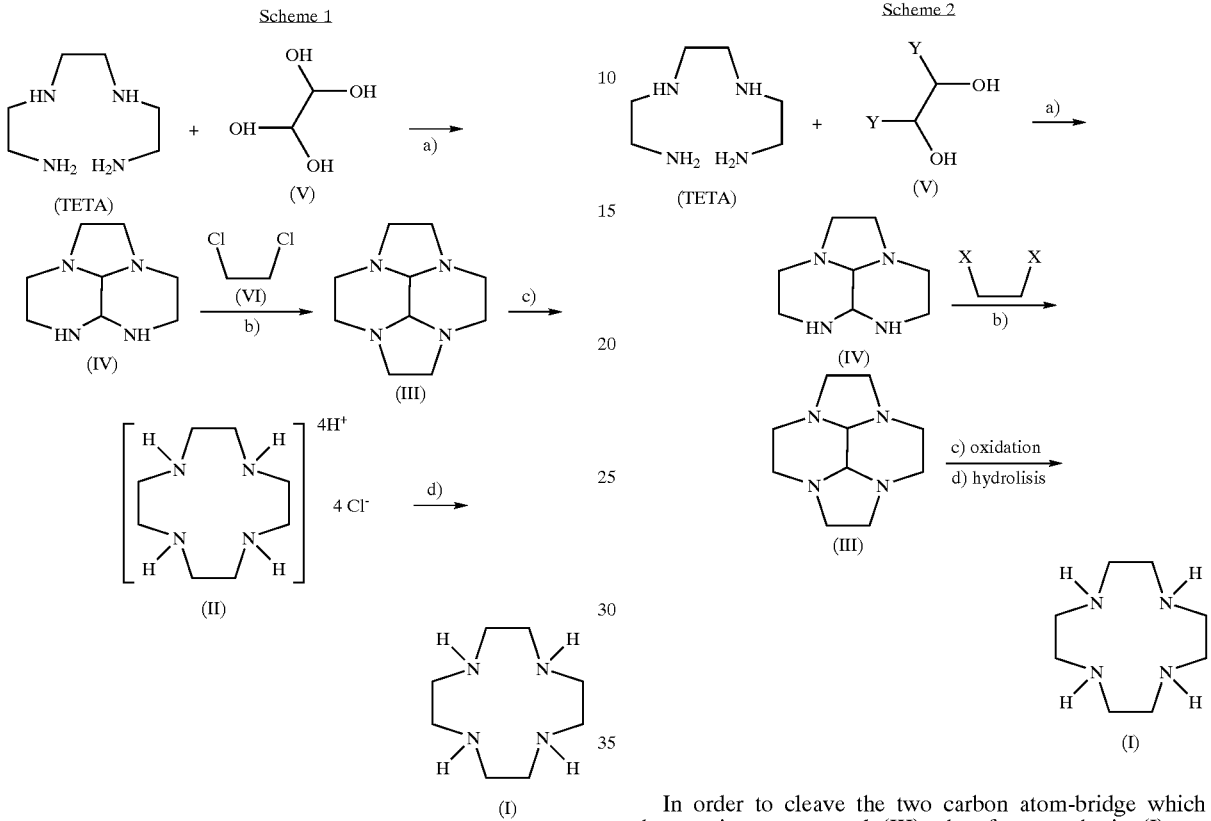

More precisely, the present invention relates to a process for the preparation of 1,4,7,10-tetraazacyclododecane (commnonly named Cyclen) alternative to the classical Richman-Atkins synthesis (see for example J. Am. Chem. Soc., 96, 2268, 1974), at present industrially used for the production of compound (I) in the form of the sulfate salt.

1,4,7,10-Tetraazacyclododecane is the precursor for the synthesis of macrocyclic chelating agents for metal ions, as these chelating agents form very stable complexes with such ions.

In particular, the complexes with the paramagnetic metal ions, specifically the gadolinium ion, of said chelaing agents can be used in the medical diagnostic field through Nuclear Magnetic Resonance technique, otherwise troublesome due to the high toxicity of the free ion.

At present, two contrast media are commercially available, namely Dotarem(R) and Prohance(R), two gadolinium complexes the chemical structure of which is based on Cyclen, while others are still under investigation.

Therefore, it is important to work out a synthetic process for the preparation of said "building block", which is cost-saving and industrially advantageous.

The process for the preparation of compound (I) should, therefore, be advantageous both from an economical and environmental point of view, avoiding the preparation of amine tosyl derivatives, commonly used in the conventional Richman-Atkins synthesis.

WO 97/49691 discloses the preparation of compound (I) by means of the steps represented in Scheme 2, in which compound of formula (III), decahydro-2a,4a,6a,8a-tetraazacyclopent[fg]acenaphthylene is the key intermediate for the formation of compound (I), and is obtainable by cyclization of the intermediate (IV), 3H,6H-octahydro-2a,5,6,8a-tetraazacenaphthylene, in its turn prepared from triethylenetetramine and glyoxal;

In order to cleave the two carbon atom-bridge which characterizes compound (III), therefore to obtain (I), an oxidizing process has been described which allows to transform (III) into oxidation products which can subsequently be hydrolysed and transformed into (I) by basic hydrolysis.

Alternatively to the oxidative cleavage, WO96/28432 suggests the direct hydrolysis of (III) with hydrobromic acid, or with hydroxylamine in ethanol solution under reflux.

On the other hand, Italian patent application MI 97A 000982, in the Applicant's name, disclosed a convenient process for the preparation of (I) starting from (III), alternative to the above one, comprising a hydrolysis step in aqueous solution, at slightly acidic, neutral or slightly basic pH, with a primary diamine of formula (VI), represented in the following Scheme 3:

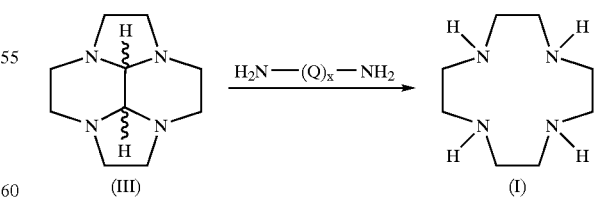

in which x ranges from 0 to 2 and Q is —CH$_2$CH(OH)CH$_2$—, —(CH$_2$)$_2$NH(CH$_2$)$_2$— or —[(CH$_2$)$_2$NH]$_2$(CH$_2$)$_2$ when x is 1 or Q is —CH$_2$— when x is 2.

Diethylenetriamine (DETA) is particularly preferred.

The reaction takes place in water, at a pH range from 5.5 to 9, preferably from 6 to 8, at temperatures from 60 to 100°

C., in the presence of 2–20 mol of diamine per mol of (III), under inert gas atmosphere or in the air, for 12–48 h.

After completion of the reaction, the solution is alkalinized with a base, such as sodium hydroxide, concentrated to small volume or to a residue, and compound (I) is extracted with a suitable solvent, such as toluene, chloroform, butanol, amyl alcohol. The organic phase is concentrated to a residue, to obtain the crude macrocycle (I), which is finally recrystallized from toluene or ethyl acetate.

However, the advantages provided by the simple combination of the two processes according to the following scheme

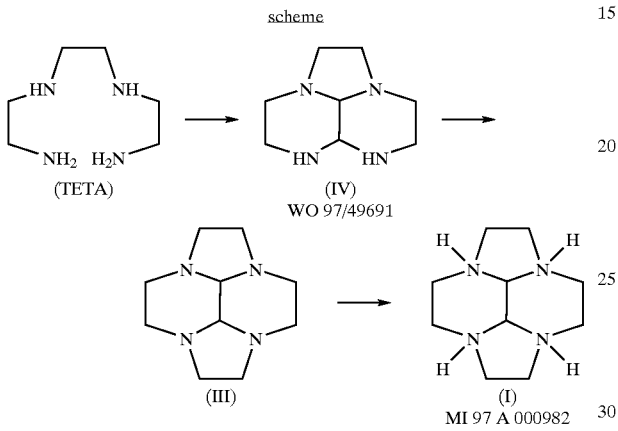

to obtain a valuable synthetic route to compound (I) are unsatisfactory, on the contrary unexpected technical problems arise, thus making their application on the factory scale difficult.

More particularly, isolation of compound (III) obtained by extraction with hexane, as described in WO 97/49691, leads to a loss of product during the concentration step of the reaction mixture, due partly to transport phenomena and partly to chemical degradation connected with the presence of parasitic alkylating agents.

In fact, as the cyclization reaction is preferential but not selective, the reaction between compound (IV) and 1,2-dichloroethane also gives rise to parasitic alkylating agents, as a consequence of side reactions of partial alkylation of said compound (IV), in amounts which cannot be ignored when operating on a large scale. These products are likely to react during the concentration step, thereby decreasing the yield in compound (III).

It has surprisingly been found that these problems can be overcome by isolating compound (III) in the form of a salt of a suitable inorganic acid.

Moreover, it has also been found that isolation of compound (I) from the reaction mixture in the form of the hydrochloride improves the industrial applicability of the process without affecting the overall yield in compound (I), as the liberation of the salt of compound (I) is quantitative.

It is therefore the object of the present invention a novel process for the preparation of compound (I) according to the following scheme 1:

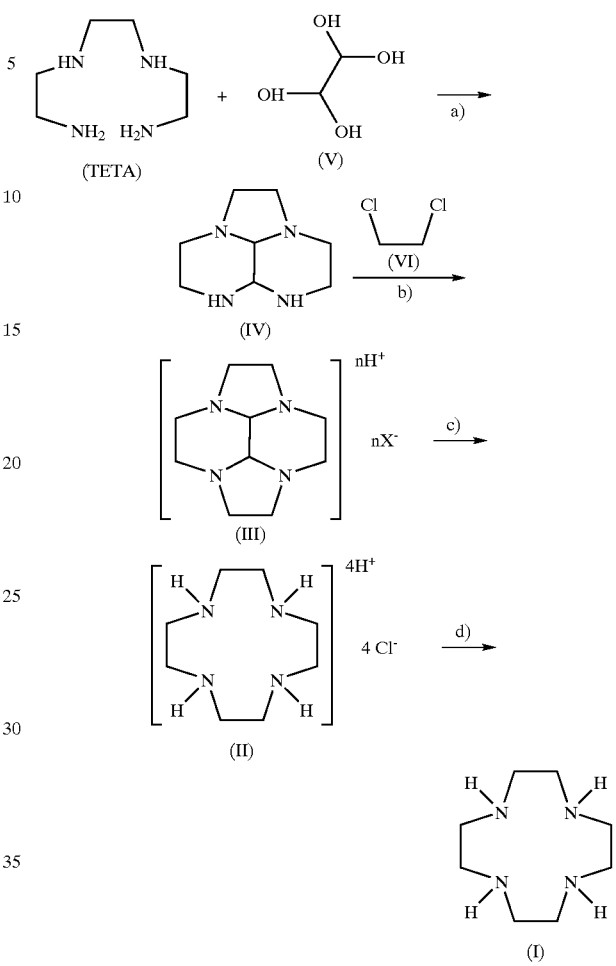

which comprises the following steps:
a) condensation of triethylenetetramine (TETA) with glyoxal hydrate in water or water-soluble solvents or mixtures thereof, at a temperature ranging from 0 to 5° C., in the presence of stoichiometric amounts or of a slight excess of calcium hydroxide, to give the compound of formula (IV);
b) reaction of compound of formula (IV) with 1,2-dichloroethane, in amounts from 1 to 5 mol per mol of compound (IV), in dimethylacetamide (DMAC) and in the presence of $Na_2CO_3$, in amounts from 5 to 10 mol per mol of compound (IV), adding NaBr in amounts from 0.1 to 2 mol per mol of compound (IV) at a temperature from 25 to 150° C., to give the compound of formula (III) which is isolated in the form of a salt of an inorganic acid selected from the group consisting of hydrochloric acid and phosphoric acid;
c) hydrolysis of compound (III) by reaction with diethylenetriamine in water, at pH ranging from 5 to 9, at a temperature ranging from 90 to 120° C., in the presence of 5–10 mols of diethylenetriamine per mol of compound (III), under inert gas atmosphere or in the air, for 12–48 h, recovering compound (II) as the tetrahydrochloride; and optionally
d) quantitative liberation of the base to give compound of formula (I).

Step a) is substantially effected as described in WO 97/49691.

Step b) is also carried out according to the method described in WO 97/49691, but preferably following a modification as illustrated in the subsequent Italian application MI 97 A000783.

In particular, in the process of the present invention, condensation of compound (III) is carried out with 3–5 mols of 1,2-dichloroethane per mol of compound (III), in DMAC, in the presence of sodium carbonate, and with the addition of NaBr as a catalyst in amounts from 0.1 to 2 mol per mol of compound (III). The preferred conditions involve 3 mol of 1,2-dichloroethane, 10 mol of sodium carbonate, and the addition of 0.5 mol of NaBr.

It has unexpectedly been found, and it is object of the present invention, that after completion of the reaction and filtration of the inorganic salts, the above mentioned problems can be overcome by addition of an acid which is both soluble in dimethylacetamide and yields a salt of compound (III) insoluble in said dipolar aprotic solvent.

Hydrochloric acid and phosphoric acid proved to be particularly suitable for this purpose.

It has been found that, by using mixtures containing compound (III) suitably diluted with DMAC and adding an amount of 37% (w/w) HCl equivalent to 2–4 mol/mol of compound (IV), preferably 2,4 mol/mol, a precipitate forms containing about 95% of compound (III) present upon completion of the reaction.

A further improvement results by replacing 37% (w/w) HCl with 85% (w/w) $H_3PO_4$, which allows to reduce the solvent amount necessary to attain the almost complete precipitation of compound (III) as a phosphate. The resulting salt is a diphosphate.

In particular, precipitation tests carried out prove evidenced that a ratio of 2 mol of $H_3PO_4$ per mol of starting compound (IV) is excellent for precipitating compound (III).

The use of 85% (w/w) $H_3PO_4$ also involves the use of less $H_2O$ compared with 37% (w/w) HCl (which has to be taken in consideration when DMAC is recovered by fractional distillation).

In order to isolate compound (III) hydrochloride, it is preferable to operate with a dilution of 6 L DMAC/mol of compound (IV), whereas in the case of diphosphate it is possible to operate in a more concentrated solution, i.e. 4.5 L DMAC/mol of compound (IV), thus decreasing the necessary amount of solvent.

Step c) is the hydrolysis, or better the deprotection of compound (III), which is the glyoxal-protected form of compound (I), according to the method described in the Italian patent application MI 97A 000982, with an amine capable of irreversibly displacing glyoxal. Diethylenetriamine (DETA) proved to be extremely productive for this purpose.

The presence of DETA, however, involves problems concerning the direct isolation of compound (I) free base from the hydrolysis mixture, which, according to the teachings of said patent application, is carried out by addition of a base until strongly alkaline pH, extraction with toluene and crystallization in suitable temperature and concentration conditions.

Following said procedure, as it will be illustrated in the Examples, when using pure compound (III), although the conversion (III)/(I) on the reaction crude is rather satisfactory, the yield in purified product is about 70% due to DETA impurities which make a further crystallization step necessary.

The separation of DETA from the reaction mixture is therefore of paramount importance for qualitative and quantitative purposes, whereas the definition of a riproducible procedure in the conversion (III)/(I) should take into account that the starting material is a reaction crude.

It has surprisingly been found that the final isolation of compound (I) in the form of the tetrachloride allows to recover more than 95% of the compound (I) resulting from the hydrolysis reaction, and it is extremely selective towards compound (I) compared with DETA and reaction impurities, yielding a highly pure product.

When necessary, the tetrachloride can be quantitatively converted into the free base according to known methods, by reaction with aqueous NaOH followed by elimination of $H_2O$ (for example by azeotropical distillation with toluene), filtration of the salts and crystallization from toluene.

The residual compound (I) present in crystallization mother liquors can be recovered as tetrachloride and recirculated without losses. The conversion (I)*4HCl/(I) can therefore be carried out quantitatively.

The (III):DETA=1:5 molar ratio is the most productive in the conversion (III) (hydrochloride or phosphate)/(I). Moreover, the purification of compound (I) as tetrachloride is not affected by the DETA amount in the reaction.

This way, the problems observed with the cited Patent are avoided, resulting in a more suitable process for the industrial scale.

The following examples illustrate the best experimental conditions to carry out the process of the invention.

EXPERIMENTAL SECTION

The following method was used for the gas-chromatographic analysis

| | |
|---|---|
| Instrumentation | Gas-chromatographic unit Hewlett-Packard series 5890 II Plus equipped with autosampler series 7673 and unit HP-3365 |
| Column | HP-ULTRA 1, 25 m, int. diam. 0.32 mm, film 0.52 $\mu$m (cod. HP no. 19091 A-112) |
| Oven temp. program | 1st isotherm at 150° C. for 0.5 min; ramp 10° C./min to 185° C.; 2nd isotherm at 185° C. for 0.01 min; ramp 20° C./min to 240° C.; 3rd isotherm at 240° C. for 2 min |
| Injector Split (spilt ratio 1:60) | |
| | Splitting flow 72 mL/min |
| | Temperature 260° C. |
| | Split insert (HP art. 18740–80190) with glass wool (Chrompack art.8490) and stationary phase Chromosorb$^{(R)}$ W HP 80–100 mesh (Supelco art. 2-0153) |
| Detection | FID |
| | Temperature 290° C. |
| Column flow | 1.2 ml/min |
| Transport gas | $He_2$ |
| Injection | 1 $\mu$l |
| Sample concentration | 10–20 mg/mL in $H_2O$ |

EXAMPLE 1

Preparation of Compound (I)

A) TETA Purification

A reactor fitted for the reaction is loaded, under nitrogen atmosphere, with 5 kg of crude TETA, then, keeping the system under stirring and under nitrogen atmosphere, 800 g of deionized water are added in 8 min keeping the system internal temperature below 45° C.

After the system has settled at 35° C., the reaction mass is added with 1 g of pure straight TETA hydrate, keeping under stirring for 1 h, then 10 L of toluene are added in 20 min. The reaction mixture is heated to 40° C., then cooled to 25° C. in 30 minutes, keeping this temperature for 30 min. The precipitate is filtered through a septum, washed with toluene and dried in a static dryer (30° C.) under vacuum (2 kPa) for 24 h. 3.71 kg of the desired product are obtained.
Yield: 89% (on anhydrous) compared with the content in linear isomer in the starting mixture.
GC assay: 98.22% (% Area)
$H_2O$ (Karl Fischer): 20.75%

B) Preparation of Compound (IV)

A reactor fitted for the reaction is loaded, under nitrogen atmosphere, with 3.71 kg of straight TETA hydrate, 20 kg of $H_2O$ and 2.9 kg of calcium hydroxide. The resulting suspension is stirred under nitrogen atmosphere and cooled to 0–5° C., then, while keeping the T of reaction at 0–5° C., is added with a 9% (w/w) glyoxal aqueous solution obtained by mixing 2.9 kg of 40% solution with 10 kg of $H_2O$.

After completion of the addition, the mixture is kept at 5° C. for 1 h, added with 1 kg of celite previously washed with $H_2O$ and left under stirring for 15 min. Calcium hydroxide is filtered off. The filtrate is concentrated with rotary evaporator under reduced pressure to a dry residue.

The product is not subjected to purification and is used as it is for the subsequent reaction.
Yield: 98.5% (on anhydrous)
GC assay: 95.5% (% Area)
$H_2O$ (Karl Fischer): 0.24%

C) Preparation of the Compound (III) as Phosphate on Pilot Scale

The reactor fitted for the reaction, pre-heated at 40° C., is loaded, under nitrogen atmosphere, with a solution of 3.48 kg of compound (IV) (prepared as described in the previous step) in 80 L of DMAC, 11.6 kg of $Na_2CO_3$:NaBr=10:1 (w/w) micronised mixture and 5.94 kg of 1,2-dichloroethane. The resulting mixture is heated to 80° C. and kept at said T for 3 h, then cooled to 25° C. and filtered through a septum, washing the salts with 10 L of DMAC. The filtrate is loaded again in the reactor.

Keeping the internal T at 20° C. and under nitrogen atmosphere, 4.61 kg of 85% (w/w) $H_3PO_4$ are added drop by drop therein. The mixture is stirred under said conditions for 2 h, then left to stand overnight. The precipitate is filtered through a septum and washed with 10 L of isopropanol. The product is then dried in a static dryer under vacuum to obtain 7 kg of crude compound (III) phosphate (content in (III) diphosphate: 65% w/w).
Yield: 58%

D) Preparation of Compound (I)

A reactor fitted for the reaction is loaded, under nitrogen atmosphere, with a solution of 7.0 kg of crude compound (III) phosphate in 14 kg of $H_2O$, 5 kg of diethylenetriamine are quickly added thereto and the resulting mixture is adjusted to pH 7 by addition of 34% HCl. The resulting mixture, stirred under nitrogen atmosphere, is refluxed and kept in said conditions for 24 h, then cooled to 25° C. and added with 10 kg of 34% HCl. The resulting solution is concentrated under reduced pressure to a weight of 30 kg.

An equal weight of 34% HCl is added thereto, stirring for at least 2 h at 25° C., then the mixture is left to stand overnight. The precipitate is filtered and washed with 20% (w/w) HCl to obtain 4 kg of a precipitate which is dissolved in 5 kg of $H_2O$ at 60° C. Insolubles are filtered off at said temperature, the solution is transferred into a reactor pre-heated at 50° C., and 7.15 kg of 34% (w/w) HCl are added in 1 h, keeping said T and stirring. The mixture is cooled to 20° C. and filtered, washed with 20% (w/w) HCl and with absolute ethanol. After drying in a static dryer under vacuum, 2.3 kg of crystalline compound (I) tetrachloride are obtained.
Yield: 36.1% (compared with compound (IV))
GC assay: 99.89% (% Area)
$H_2O$ (K.F.): 0.18%
Acidic titer (0.1 N NaOH): 98.9%
Argentometric titer (0.1 N $AGNO_3$): 99.98%
Complexometric titer (0.1 N $ZnSO_4$) 98.6%
$^1$H-NMR, $^{13}$C-NMR, IR and MS spectra are consistent with the indicated structure.

EXAMPLE 2

Isolation of Compound (III) as Crude Hydrochloride

The preparation of compound (III) hydrochloride is carried out substantially as in step C) of Example 1, except that no final drying is carried out. Concentrated hydrochloric acid is used instead of phosphoric acid. At the end of the isolation, the humid product is not subjected to drying but it is directly analyzed for the determination of the content in (III). The yields under various isolation conditions are reported in table 1.

TABLE I

Isolation of compound (III) as crude hydrochloride.

| Compound (IV) | | | | |
|---|---|---|---|---|
| Kg | mol | DMAC (L) | mol HCl/(IV) | % yield |
| 0.64 | 3.9 | 23.4 | 2.41 | 46 |
| 2.5 | 15 | 90 | 2.41 | 51 |
| 2.5 | 15 | 90 | 2.41 | 49 |

EXAMPLE 3

Isolation of Compound (III) as Crude Phosphate

TABLE II

| Compound (IV) | | | | |
|---|---|---|---|---|
| Kg | Mol | DMAC (L) | mol $H_3PO_4$/(IV) | % yield |
| 0.33 | 2 | 12 | 2.4 | 53 |
| 0.98 | 6 | 36 | 2.4 | 52 |
| 0.90 | 5.5 | 54 | 1 | 41 |
| 2.5 | 15 | 67.5 | 2 | 58 |
| 2.5 | 15 | 67.5 | 4 | 49 |

What is claimed is:

1. A process for the preparation of 1,4,7,10-tetraazacyclododecane, said process comprising the steps of:

a) condensing triethylenetetramine with glyoxal hydrate in water or water-soluble solvents or mixtures thereof, at a temperature ranging from 0 to 5° C., in the presence of stoichiometric amounts or of a slight excess of calcium hydroxide, to give the 3H,6H-octahydro-2a,5,6,8a-tetraazacenaphthylene;

b) reacting 3H,6H-octahydro-2a,5,6,8a-tetraazacenaphthylene with 1,2-dichloroethane, in an amount from 1 to 5 mol per mol of 3H,6H-octahydro-2a,5,6,8a-tetraazacenaphthylene, in dimethylacetamide and in the presence of $Na_2CO_3$, in an amount from 5 to 10 mol per mol of 3H,6H-octahydro-2a,5,6,8a-tetraazacenaphthylene, adding NaBr in an amount from 0.1 to 2 mol per mol of 3H,6H-octahydro-2a,5,6,8a-tetraazacenaphthylene at a temperature from 25 to 150° C., to give decahydro-2a,4a,6a,8a-tetraazacyclopent[fg]acenaphthylene, adding an inorganic acid selected from the group consisting of hydrochloric acid and phosphoric acid, and isolating decahydro-2a,4a,6a,8a-tetraazacyclopent[fg]acenaphthylene in the form of a salt;

c) hydrolyzing decahydro-2a,4a,6a,8a-tetraazacyclopent[fg]acenaphthylene by reaction with diethylenetriamine in water, at pH ranging from 5 to 9, at a temperature ranging from 90 to 120° C., in the presence of 5–10 mols of diethylenetriamine per mol of decahydro-2a,4a,6a,8a-tetraazacyclopent[fg]acenaphthylene, in an inert gas atmosphere or in air, for 12–48 hours, recovering the hydrolyzed product as the tetrahydrochloride by adding hydrochloric acid; and optionally d) quantitatively liberating the base to give 1,4,7,10-tetraazacyclododecane.

2. The process as claimed in claim 1, in which condensation of decahydro-2a,4a,6a,8a-tetraazacyclopent[fg]acenaphthylene in step (b) is carried out with 3–5 mol of 1,2-dichloroethane per mol of decahydro-2a,4a,6a,8a-tetraazacyclopent[fg]acenaphthylene, in dimethylacetamide, in the presence of sodium carbonate, and with the addition of NaBr as a catalyst in an amount from 0.1 to 2 mol per mol of decahydro-2a,4a,6a,8a-tetaazacyclopent[fg]acenaphthylene.

3. The process as claimed in claim 2, in which 3 mol of 1,2-dichloroethane, 10 mol of sodium carbonate and 0.5 mol of NaBr are used.

4. The process according to claim 1, 2 or 3, in which the final reaction mixture from step (b) is added with an amount of concentrated HCl equivalent to 2–4 mol/mol of 3H,6H-octahydro-2a,5,6,8a-tetraazacenaphthylene.

5. The process as claimed in claim 4, wherein the concentration of the solution is 6 L of dimethylacetamide/mol of 3H,6H-octahydro-2a,5,6,8a-tetraazacenaphthlene.

6. The process according to claims 1, 2 or 3, in which the final reaction mixture from step (b) is added with an amount of 85% $H_3PO_4$ equivalent to at least 2 mol/mol of 3H,6H-octahydro-2a,5,6,8a-tetraazacenaphthylene.

7. The process as claimed in claim 6, wherein the concentration of the solution is equivalent to 4.5 L of dimethylacetamide/mol of 3H,6H-octahydro-2a,5,6,8a-tetraazacenaphthylene.

8. The process according to claim 1, in which in step (c) the molar ratio of salt of decahydro-2a,4a,6a,8a-tetraazacyclopent[fg]acenaphthylene to diethylenetriamine is 1:5.

* * * * *